(12) United States Patent
Sonohata et al.

(10) Patent No.: US 8,162,995 B2
(45) Date of Patent: Apr. 24, 2012

(54) BONE PLATE

(75) Inventors: Motoki Sonohata, Saga (JP); Takao Hotokebuchi, Saga (JP); Masaru Kitajima, Saga (JP)

(73) Assignee: Saga University, Saga (JP)

( * ) Notice: Subject to any disclaimer, the term of this patent is extended or adjusted under 35 U.S.C. 154(b) by 820 days.

(21) Appl. No.: 12/087,576

(22) PCT Filed: Mar. 17, 2006

(86) PCT No.: PCT/JP2006/305426
§ 371 (c)(1),
(2), (4) Date: Jul. 10, 2008

(87) PCT Pub. No.: WO2007/108074
PCT Pub. Date: Sep. 27, 2007

(65) Prior Publication Data
US 2009/0030467 A1 Jan. 29, 2009

(51) Int. Cl.
*A61B 17/80* (2006.01)
(52) U.S. Cl. ......... 606/280; 606/281; 606/286; 606/297
(58) Field of Classification Search .......... 606/280, 606/281, 286, 105, 101, 86 B, 915, 205–209, 606/282, 283, 86 R
See application file for complete search history.

(56) References Cited

U.S. PATENT DOCUMENTS

| | | | | |
|---|---|---|---|---|
| 5,344,421 A | * | 9/1994 | Crook | 606/281 |
| 6,793,658 B2 | * | 9/2004 | LeHuec et al. | 606/86 B |
| 7,074,221 B2 | * | 7/2006 | Michelson | 606/70 |

OTHER PUBLICATIONS

AO Publishing, Ruedi, Thomas P. & Murphy, William M., "AO Principles of Fracture Management" pp. xiv-xvii 174-150, 169-177, 2000.
Springer-Verlag, Heim & U Pfeiffer, K. M., "Internal Fixation of Small Fractures" pp. 20-31.

* cited by examiner

*Primary Examiner* — Thomas C. Barrett
*Assistant Examiner* — Andrew Yang
(74) *Attorney, Agent, or Firm* — Rader, Fishman & Grauer PLLC

(57) ABSTRACT

A bone plate having a rear face and opposing front face, adapted to be abutted on a bone, and a through hole extending between the front and rear faces, and attached to a bone to be set by applying the bone plate to the bone, and by screwing a screw into the bone through the through hole. The bone plate has a blind first dimple provided in at least one of the faces thereof other than the rear face. One acute gripping tip of a pair of bone forceps may be abutted on the bone, with the other acute griping tip of the bone forceps being engaged in the first dimple. The first dimple is configured so as to converge from an opening portion thereof on the dimple-provided face toward a bottom portion thereof, whereby the other acute gripping tip of the bone forceps can slide toward the bottom portion.

6 Claims, 12 Drawing Sheets

BONE PLATE

TECHNICAL FIELD

The present invention relates to a bone plate which can be held by a pair of bone forceps.

BACKGROUND OF ART

In a conventional plate, a plurality of screw holes for insertion of screws are formed (see: for example, Non-Patent Document 1 and Non-Patent Document 2).

Also, in order to temporarily fix the plate to a bone, a pair of reduction forceps having serrated flanges are used (see: for example, Non-Patent Document 1 and Non-Patent Document 2).

Non-Patent Document 1: "AO Principals of Fracture Management" by Editor in Chiefs, Thomas P. Ruedi and William M. Murphy, General Japanese Edition by Seiken ITOMAN, First Version, published by IGAKU-SHOIN Ltd. Mar. 15, 2003, p. 111, 130-135

Non-Patent Document 2: "Internal Fixation of Small Fracture Operation technique of AO-ASIF Group" by Urs Heim and Karl M. Pfeiffer, Supervised and Translated by Seiichi ISHII, First Version, published by Springer Verlag Tokyo Kabushiki Kaisha, Nov. 1, 1989, p. 23-25, 32

DISCLOSURE OF THE INVENTION

Problems to be Resolved by the Invention

When the serrated reduction forceps, as disclosed in Non-Patent Document 1 and Non-Patent Document 2, are used to temporary fixation of a plate to a bone, the bone and the plate are gripped by both the serrated tooth portions of the reduction forceps, and thus there is a problem that peelings of soft tissues may occur over large extents corresponding to a size of the flanges of the reduction forceps.

Also, since a surface of the plate is not formed as an uneven surface except for locations at which through holes are perforated, the surface of the plate cannot be bitten by the tooth portions of the reduction forceps, and thus there is a problem that the gripping of the bone and the plate is apt to be loosened.

Also, although a pair of reduction forceps (which will be referred to as bone forceps, hereinafter) having acute tips, which is inherently use to grip a bone, is utilized to grip the bone and the plate, it is impossible to held the surface of the plate by one of the tips of the bone forceps due to the fact that the surface of the plate is not formed as the uneven surface except for the locations at which the through holes are perforated, and thus there is a problem that the gripping of the bone and the plate is difficult. Especially, when the plate has a specular-finished surface so that soft tissues can be easily peeled from the plate during a nail-removal operation, it is difficult to grip the bone and the plate by the bone forceps having the acute tips.

The present invention has been achieved to solve the above-mentioned problems, and an object of the present invention is to provide a bone plate which is constituted so that a bone and a plate can be securely gripped even when the gripping of the bone and the plate is carried out by using a pair of bone forces by which a soft-tissue peeling extent can be narrowed in comparison with a pair of serrated reduction forceps.

Means for Solving the Problems

A bone plate according to the present invention has a first dimple provided in at least one of faces thereof except for a rear face thereof, and the first dimple is configured so as to converge from an opening portion thereof on the dimple-provided face toward a bottom portion thereof.

EFFECT OF THE INVENTION

According to the present invention, since the bone plate has the first dimple provided in at least one of the faces thereof except for the rear face thereof, and since the first dimple is configured so as to converge from the opening portion thereof on the dimple-provided face toward the bottom portion thereof, one of tips of a pair of bone forceps can be engaged in the first dimple, and then the tip thus engaged can be made to slide on a sloped face so as to be guided toward and fixed on the bottom portion, whereby a bone and the bone plate can be gripped by the bone forceps.

BRIEF EXPLANATIONS OF DRAWINGS

EXPLANATION OF REFERENCES

1 Bone Plate
1a Rear Face

1b Front Face
1c Side Face
2 Through Hole
2a Concave Seat Face
2b Female Thread
3 First Dimple
3a Opening Portion
3b Bottom Portion
3c Inner Face
4 Screw
4a Head Portion
4b Male Thread
5 Fracture Line
6 Diaphysis Portion
7 Bone Forceps
7a, 7b Tip
7c Fulcrum
8 Second Dimple
8a Opening Portion
8b Inner Face
9 Longitudinal Groove
10 Biological Biodegradable/Bioabsorbable Membrane

THE BEST MODE FOR EMBODYING THE INVENTION

Embodiment Mode 1

Figure 1:
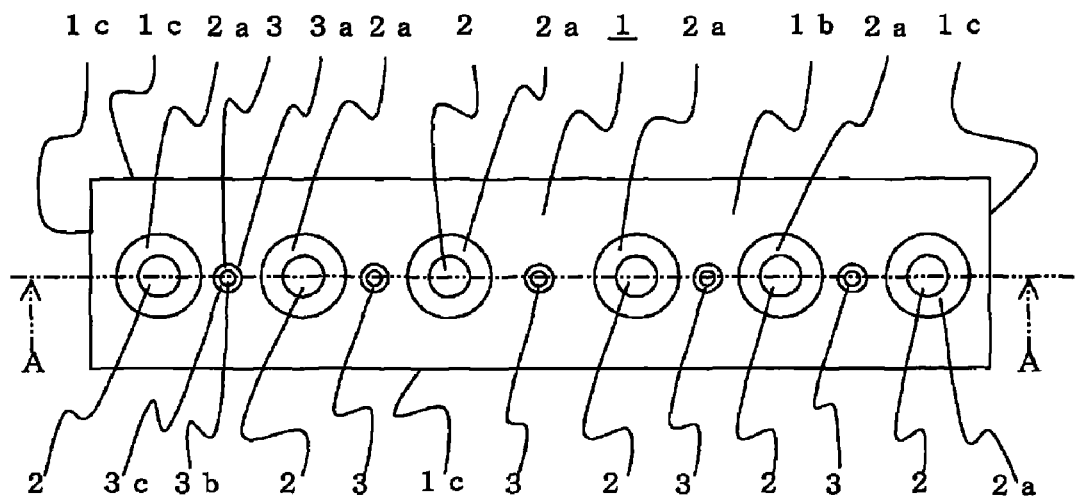
FIG. 1 are views showing a bone plate of Embodiment Mode 1 for embodying the present invention, (a) being a top view, (b) being a bottom view.
Figure 1:
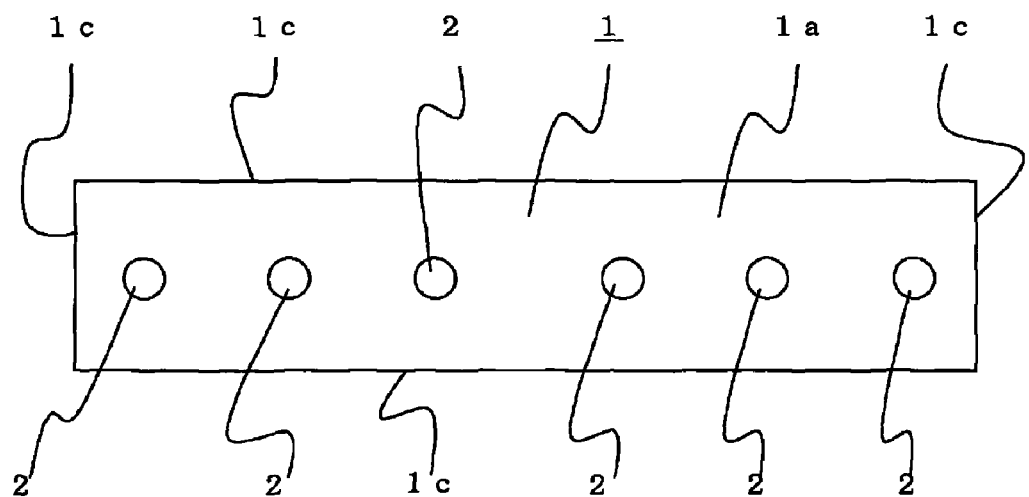
Figure 2:
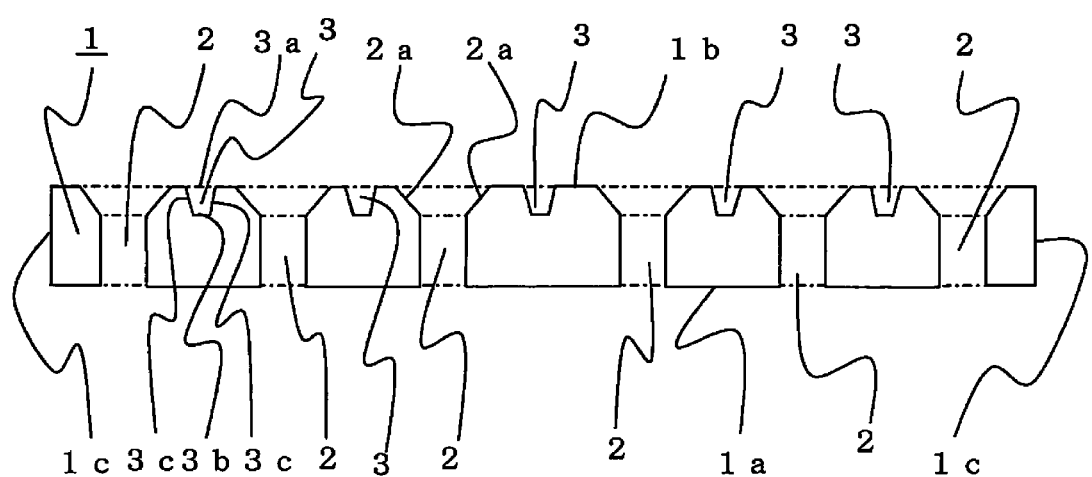
FIG. 2 is a cross-sectional view taken along the A-A line of the bone plate shown in FIG. 1.
Figure 3:
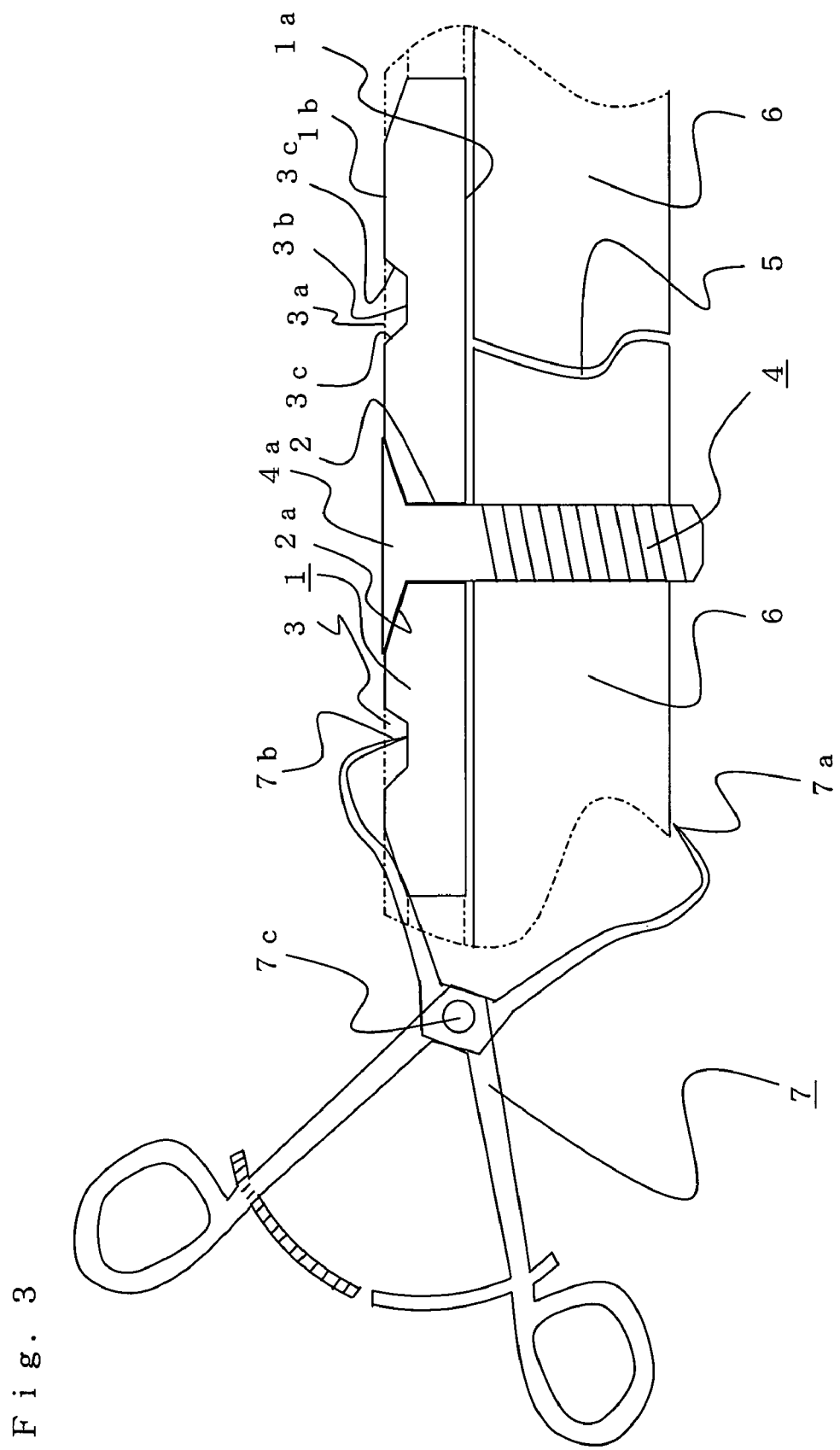
FIG. 3 is an explanatory view for explaining a function of first dimples provided in the bone plate shown in FIG. 1.
Figure 4:
FIG. 4 are views showing the first dimples in which each bottom portion is defined as a converging point of an inner face, (a) being a perspective view showing an example, (b) being a perspective view showing another example.
Figure 4:
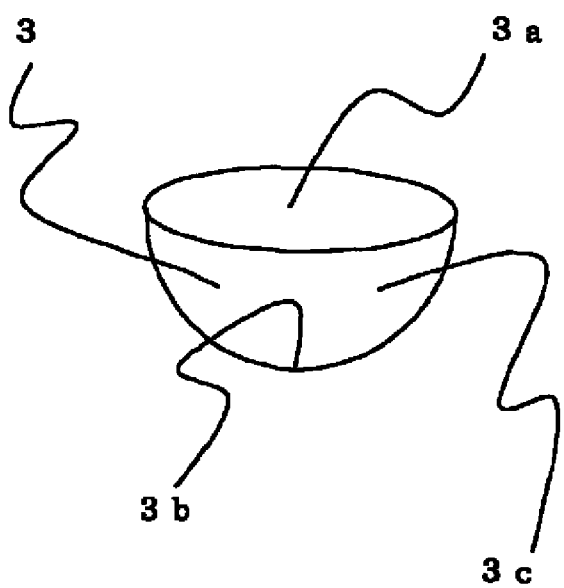
Figure 5:
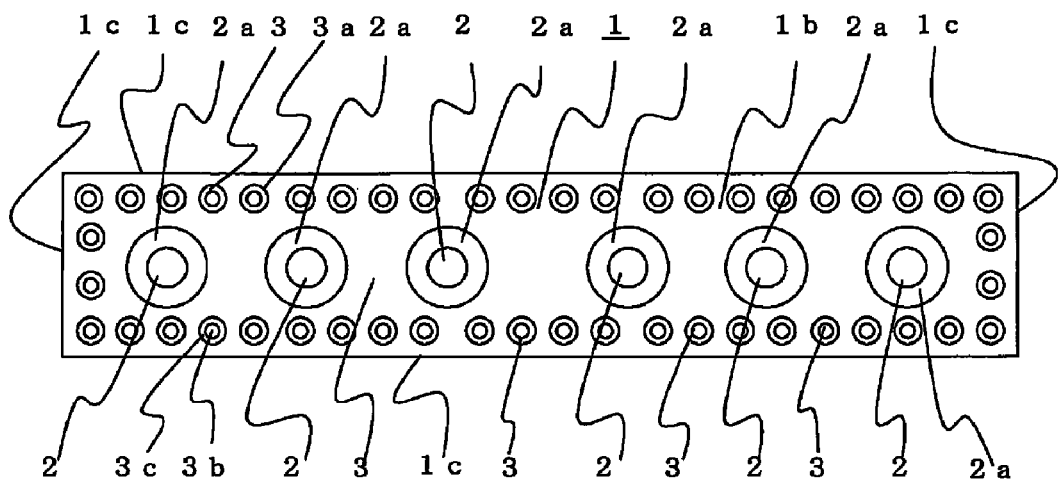
FIG. 5 shows arrangements of the first dimples, (a) being a top view showing the bone plate in which the first dimples are arranged along sides thereof, (b) being a top view showing the bone plate in which the first dimples are concentrically arranged around a center of each of through holes.
Figure 5:
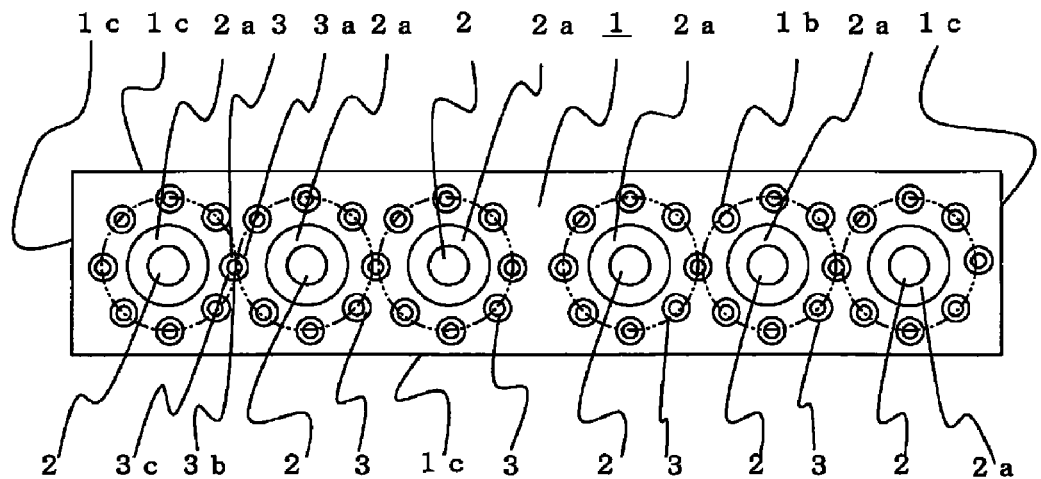
Figure 6:
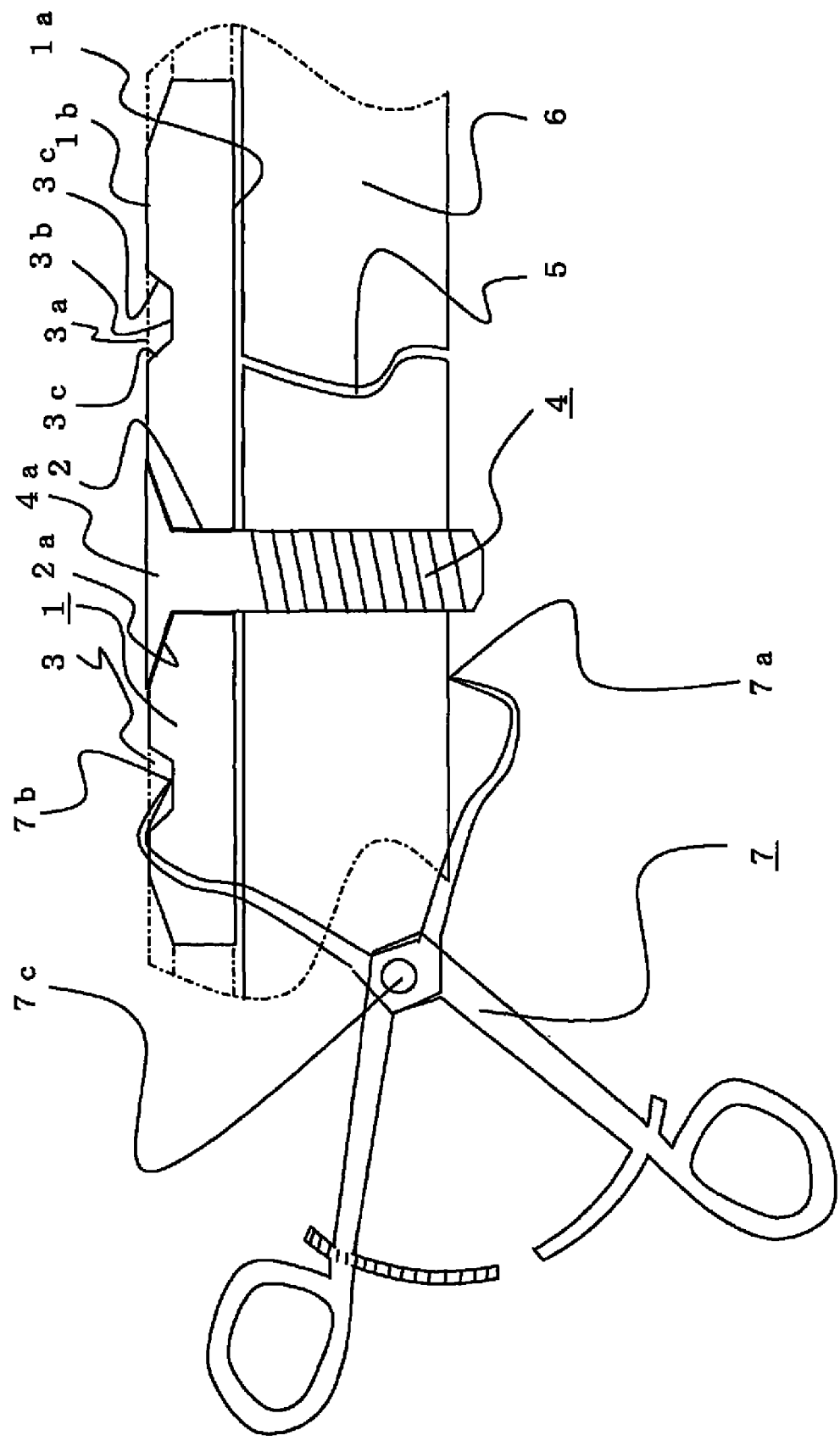
FIG. 6 is an explanatory view for explaining a function of the first dimples provided in the bone plate shown in FIG. 1.
Figure 7:
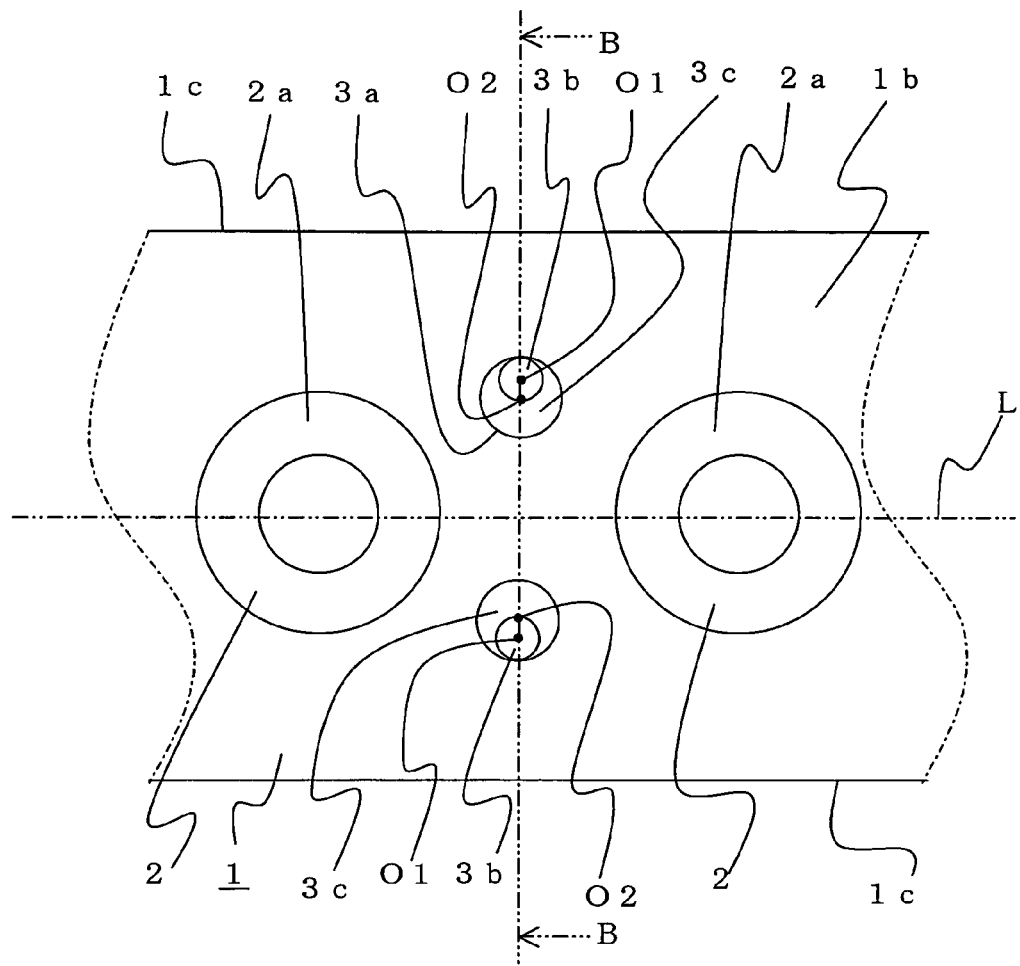
FIG. 7 are views showing another bone plate of Embodiment Mode 1 for embodying the present invention, (a) being a partially-enlarged top view, (b) being a cross-sectional view taken along the B-B line of the bone plate shown in FIG. 7(a).
Figure 7:
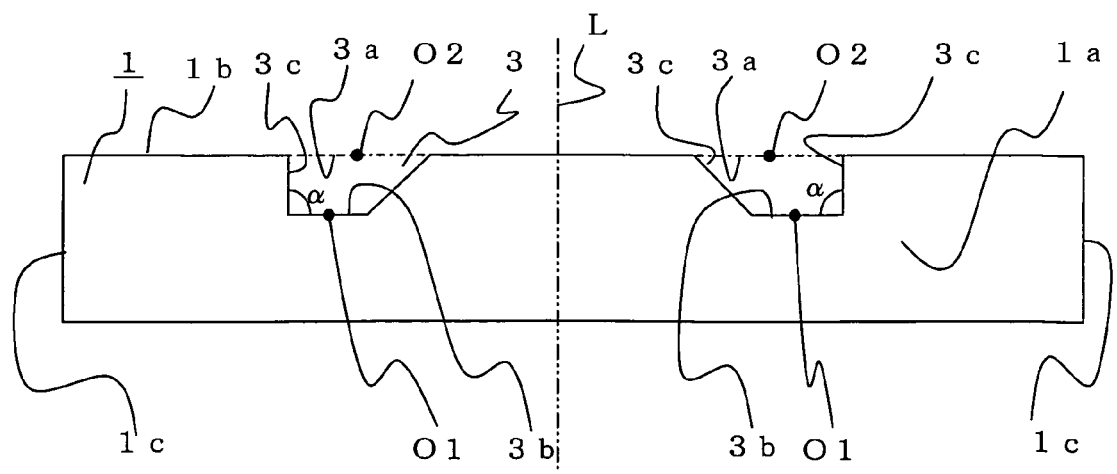
Figure 8:
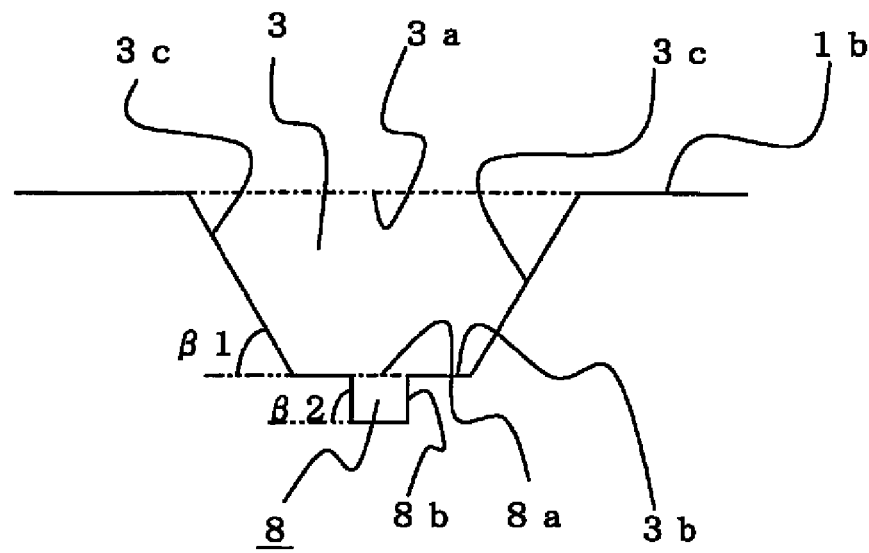
FIG. 8 shows the first dimples in which second dimples are provided in respective bottom portions thereof, (a) being a cross-sectional view showing an example, (b) being a cross-sectional view showing another example.
Figure 8:
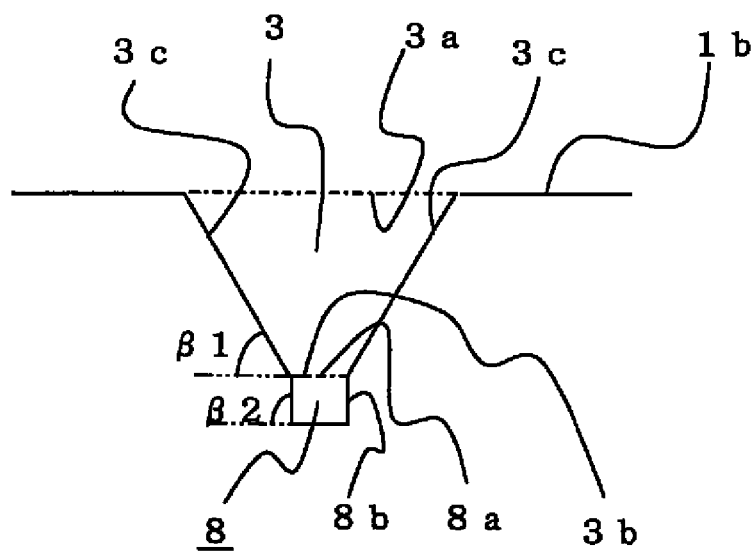
Figure 9:
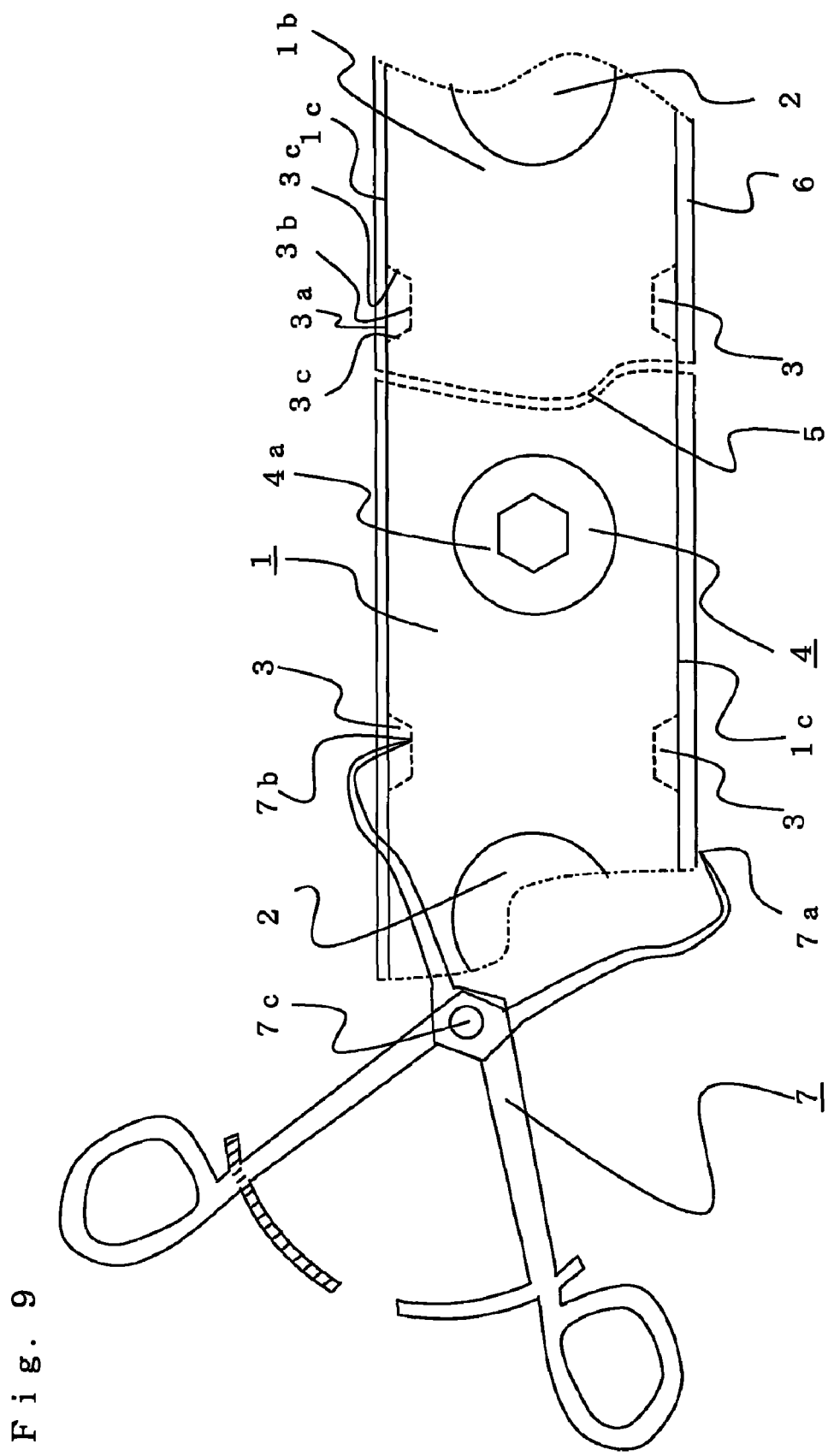
FIG. 9 is an explanatory view for explaining a function of the first dimples provided in side faces of the bone plate.

FIG. 1(a) is the top view showing a bone plate of Embodiment Mode 1 for embodying the present invention, FIG. 1(b) is the bottom view showing the bone plate of Embodiment Mode 1 for embodying the present invention, FIG. 2 is the cross-sectional view taken along the A-A line of the bone plate shown in FIG. 1, FIG. 3 is the explanatory view for explaining a function of first dimples provided in the bone plate of FIG. 1, FIG. 4(a) is the perspective view showing an example of the first dimple in which a bottom portion is defined as a converging point of an inner face, FIG. 4(b) is the perspective view showing another example of the first dimple in which a bottom portion is defined as a converging point of an inner face, FIG. 5(a) is the top view showing the bone plate in which the first dimples are arranged along sides thereof, FIG. 5(b) is the top view showing the bone plate in which the first dimples are concentrically arranged around a center of each of through holes, FIG. 6 is the explanatory view for explaining a function of the first dimples provided in the bone plate shown in FIG. 1, FIG. 7(a) is the partially-enlarged top view showing another bone plate of Embodiment Mode 1 for embodying the present invention, FIG. 7(b) is the cross-sectional view taken along the B-B line of the bone plate shown in FIG. 7(a), FIG. 8(a) is the cross-sectional view showing an example of the first dimple in which a second dimple is provided in a bottom portion thereof, FIG. 8(b) is the cross-sectional view showing another example of the first dimple in which a second dimple is provided in a bottom portion thereof, and FIG. 9 is the explanatory view for explaining a function of the first dimples provided in side faces of the bone plate.

In FIGS. 1-9, a bone plate 1 is defined by a rear face 1a adapted to be applied to a bone, a front face 1b opposed to the rear face 1a, side faces 1c coupling the sides of the front face 1a to the sides of the rear face 1a, and has a plurality of through holes 2 passing through the front face 1b and the rear face 1b, with the bone plate being applied to a bone to be attached through the intermediary of the through hole 2. Also, the bone plate 1 is composed of a metal material exhibiting a high rigidity, a superior ductility and an organism affinity, and is formed of a monolithic thin metal plate as a whole. For the metal material, although there is stainless steel or titanium for the metal material, it is preferable to use pure titanium or titanium alloy exhibiting a coefficient of elasticity near to that of bone.

Note, in this Embodiment Mode 1, although a configuration of the bone plate 1 is referred to as a rectangular parallelepiped defined by the front face 1b and the rear face 1a, each of which is shaped as a rectangle, and the four side faces 1c, the bone plate should not be limited to only the rectangular parallelepiped, and it is possible to obtain similar advantages by forming first dimples 3, as stated hereinafter, in a plate having a variety of configuration. As an example of the configuration of the plate, there are: a one-third circular plate which is useful to be covered with a soft tissue at a minimum space; a plate having a through hole for making axial compression possible by insertion of an eccentric screw; a plate for reducing a contact area the plate and a bone; a plate having a deep groove formed in a side face between through holes adjacent to each other; or a plate having a shape (T-, L-, H-, clover-shape or the like) formed for a specific region.

Although the bone plate 1 may have at least one through hole 2 formed therein, in this embodiment mode, the six through holes 2 are formed so as to be aligned with each other in a longitudinal direction of the bone plate 1 at given regular intervals. A concave seat face 2a is formed at the side of the through hole 2 into which a screw 4 is inserted, so that a head portion 4a of the screw 4 is fittingly received in the concave seat face 2a. Although this concave seat face 2a may be formed as a mere tapered face, it may be formed as a spherical face so as to be conformed with a shape of the head portion 4a. Also, in a case where the screw 4a, the head 4 of which has a male thread formed therearound, is used, the screw 4 can be threadedly engaged with the concave seat face 2a by forming a female thread in the concave seat face 2a. Note that it is possible to optionally change the number, the shape and the location of the through holes 2.

Each of the first dimples 3 is provided in the front face 1b of the bone plate 1, and is formed as a blind bore converging from an opening portion 3a, sited on the dimple-provided face of the bone plate 1, toward a bottom portion 3b sited in the interior of the bone plate 1. Note, in Embodiment Mode 1, the opening portion 3a and the bottom portion 3b of the first dimple 3 are circular in shape, and an inner face 3c coupling the edge of the opening portion 3a to the edge of the bottom portion 3b is sloped with respect to the bottom portion 3b so that a cross-sectional shape of the first dimple 3 taken along a vertical plan to the bottom portion 3b become a trapezoid.

Also, although the first dimples 3 may be formed in at least one of the faces except for the rear face 1a, in Embodiment Mode 1, the face, in which the first dimples are formed, is the front face 1b of the bone plate 1, and each of the first dimples 3 is provided at substantially a center between the through holes 2 adjacent to each other. Note that it is possible to optionally change the number, the shape and the location of the first dimples 3.

Next, a function of the first dimples 3 of the bone plate 1 in a bone-setting operation is explained.

As shown in FIG. 3, for example, it is assumed that that a diaphysis portion 6 is broken as indicated by a fracture line 5.

First, a body is dissected in vicinity of the fracture to expose the diaphysis portion 6, and the bone plate 1 is introduced into the dissected portion toward the exposed diaphysis portion 6. At this time, the rear face 1a of the bone plate 1 are applied to the diaphysis portion 6, and the bone plate 1 is positionally adjusted so as to bridge the fracture line 5 of the diaphysis portion 6.

Then, a preliminary bore for inserting the screw 4 is perforated in the diaphysis portion 6 by using a not illustrated perforation tool such as a drill or the like. At this time, the bone plate 1 and the diaphysis portion 6 are held by a pair of bone forceps 7, and thus the bone plate 1 is prevented from being moved with respect to the diaphysis portion 6 while the perforation tool is manipulated.

In particular, one tip 7a of the two tips 7a and 7b of the bone forceps 7 is abutted on the diaphysis portion 6, and the other tip 7b is abutted on the bottom portion 3b or the inner face 3c of the first dimple 3 of the bone plate 1. Although the tip 7b of the bone forceps 7 is abutted on the inner face 3c, it slips on the sloped inner face 3c toward the bottom portion 3b, resulting in stabilization of the tip 7b of the bone forceps 7 on the bottom portion 3b, and thus the tip 7b of the bone forceps 7 can be held on the bone plate 1.

Then, the screw 4 is inserted into the preliminary bore of the diaphysis portion 6 through the intermediary of the through hole 2, and is then screwed into the diaphysis portion 6 by manipulating a not illustrated tool such as a driver or the like, with the tool being engaged with a groove formed in a head portion 4a of the screw 4. At this time, similarly, the bone plate 1 and the diaphysis portion 6 are held by the bone forceps 7, and thus the bone plate 1 is prevented from being moved with respect to the diaphysis portion 6 while the tool is manipulated.

Note, in Embodiment Mode 1, although the first dimple 3 is formed so that each of the opening portion 3a and the bottom portion 3b of the first dimple 3 has the circular shape, the shape of each of the opening portion 3a and the bottom portion 3b should not be limited to the circular, and the tip 7b of the bone forceps 7 can be engaged with the opening portion 3a of the first dimple 3 as long as the opening portion 3a of the first dimple 3 is larger than the tip 7b of the bone forceps 7. For example, the shape of each of the opening portion 3a and the bottom portion 3b may be a polygon such as a square and so on or an ellipse.

Also, although the first dimple 3 is formed so as to have the trapezoid cross-sectional shape in the vertical plan to the bottom portion 3b, upon abutting the tip 7b of the bone forceps 7 on the inner face 3c, the tip 7b of the bone forceps 7 can slip on the inner face 3c toward the bottom portion 3b, resulting in abutment of the tip 7b against the bottom portion 3b, as long as the inner face 3c of the first dimple 3 is sloped with respect to the bottom portion 3b. For example, the opening portion 3a and the bottom portion 3b may be arranged not so as to be in parallel to each other, or the inner face 3c may be curved so that a side of the inner face 3c in a cross-sectional shape of the first dimple 3 in the vertical plan to the bottom portion 3b defines a part of a parabola.

Also, the first dimple 3 may be formed so that the bottom portion 3b of the first dimple 3 is defined as a converging point of the inner face 3c of the first dimple 3. Namely, by varying the bottom portion 3b of the first dimple 3 from the face to the point, the tip 7b of the bone forceps 7 can be prevented from being moved on the bottom portion 3b, and thus it is possible to securely hold the bone and the bone plate 1. For example, as shown in FIG. 4(a), the first dimple 3 may be formed as a cone shape in which the opening portion 3a, the bottom portion 3b and the inner face 3c are defined as a bottom, an apex and a cone surface, respectively. Also, as shown in FIG. 4(b), the first dimple 3 may be formed as a hemispherical shape in which the opening portion 3a, the bottom portion 3b and the inner face 3c are defined as a bottom, a point and a hemispherical surface, respectively.

Also, in Embodiment Mode 1, although each of the first dimples 3 is formed in the front face 1b of the bone plate 1 so as to be arranged at substantially the center between the through holes 2 adjacent to each other, the invention should not be limited to only this arrangement. For example, as shown in FIG. 5(a), the first dimples 3 may be arranged on the front face 1b of the bone plate 1 along the sides thereof. Also, the first dimples 3 may be concentrically arranged near each of the through holes 2 around a center thereof, whereby the tip 7b of the bone forceps 7 can held by one of the first dimples 3 arranged near the through hole 2 through which the screw 4 passes when the screw 4 is screwed into the bone through the intermediary of the through hole 2 concerned, so that it is possible to carry our the screwing of the screw 4 into the bone due to the sufficient gripping force thus obtained.

Note, in the above-mentioned bone-setting operation, as shown in FIG. 3, although the function of the first dimples 3 of the bone plate 1 is explained in the situation in which the relatively easy gripping can be obtained due to the fact that the tip 7b of the bone forceps 7 is engaged in the first dimple 3 at a nearly vertical angle to the bottom portion 3b of the first dimple 3, there may be a case where the tip 7b of the bone forceps 7 is engaged in the first dimple 3 at a parallel-like angle to the bottom portion 3b of the first dimple 3, as shown in FIG. 6.

In this case, the gripping force, which is obtained by the bone forceps 7 at the tip 7b thereof, is decomposed into a horizontal force component and a vertical force component with respect to the bottom portion 3b of the first dimple 3, and the horizontal force component may cause a sliding of the tip 7b on the bottom portion 3b toward the boundary between the bottom portion 3b and the inner face 3c. Further, the horizontal force component, which is attenuated due to the friction force on the bottom portion 3b, is decomposed into a horizontal force component and a vertical force component with respect to the inner face 3c, and this horizontal force component may cause a sliding of the tip 7b on the inner face 3c toward the opening portion 3a. Thus, there may be a case where the tip 7b of the bone forceps 7 comes out of the opening portion 3a so that the bone plate 1 and the diaphysis portion 6 cannot be held. Note, in FIG. 3, since an acting direction of the griping force by the bone forceps 7 is substantially vertical with respect to the bottom portion 3b, the horizontal force component on the bottom portion 3b is small, and is attenuated due to the friction force on the bottom portion 3b or the inner face 3c, so that the resultant force, which is obtained by the bone forceps 7 at the tip 7b thereof, is balanced so as to fix the tip 7b of the bone forceps 7 on the bottom portion 3b.

By contrast, as shown in FIGS. 7(a) and 7(b), centers O1 of the bottom portions 3b of the first dimples 3 are arranged near to the sides of the side faces 1c of the bone plate 1, which are in parallel to and symmetrical with the longitudinal direction of thereof, with respect to centers O2 of the opening portions 3a of the first dimples 3. Thus, in comparison with the first dimple 3 of FIG. 3, an angle α, which is defined by the bottom portion 3b and the inner face 3c, can be made small in a direction in which the tip 7b of the bone forceps 7 slides on the bottom portion 3b toward a boundary between the bottom portion 3b and the inner face 3c, whereby a horizontal force component on the inner face 3c can be reduced. Accordingly, it is possible to restrain the tip 7b of the bone forceps 7 from coming out of the opening portion 3a, whereby the bone plate 1 and the diaphysis portion 6 can be securely held.

Note, in FIGS. 7(a) and 7(b), in a case where the tip 7b of the bone forceps 7 is engaged in a first dimples 3, assuming that the tip 7b of the bone forceps 7 is engaged in the first dimple 3 placed at an opposite side to a fulcrum 7c of the bone forceps 7 with respect to an imaginary reference plan L which is in parallel to the side faces 1c opposed to each other in the vertical direction to the longitudinal direction of the bone plate 1, and which is placed at an equal distances from the side faces 1c concerned, the first dimples 3 are formed so as to be narrowed toward the respective side faces 1c of the bone plate 1. Thus, provided that the tip 7b of the bone forceps 7 is engaged in the first dimple 3 placed in the opposite side to the fulcrum 7c of the bone forceps 7, it is possible to obtain the advantages derived from the aforesaid angle α of the first dimple 3 although the bone plate 1 and the bone are held by the bone forceps 7 at either of the side faces 1c opposed to each other in the vertical direction to the longitudinal direction of the bone plate 1.

By contrast, if the tip 7b of the bone forceps 7 is engaged in the first dimple 3 placed in the side of the fulcrum 7c of the bone forceps 7, by arranging the center O1 of the bottom portion 3b of the first dimple 3 in the opposite side to the fulcrum 7c of the bone forceps 7 with respect to the center O2 of the opening portion 3a of the first dimple 3, it is possible to obtain the advantages derived from the aforesaid angle α of the first dimple 3.

Accordingly, it is preferable that various first dimples 3, in which the centers O1 of the bottom portions 3b are arranged in the sides of the side faces and the side of the imaginary plan L with respect to the centers O2 of the opening portion 3a, are mingled in the bone plate 1, so that the bone plate can be held in the sides of the side faces thereof by the bone forceps 7, and so that it is possible to deal with a case where the tip 7b is engaged in one of the first dimples 3 which are placed in the side of the fulcrum 7c of the bone forceps 7 and the opposite side to the fulcrum 7c of the bone forceps 7.

Also, as shown in FIGS. 8(a) and 8(b), by providing a second dimple 8 in the bottom portion 3b of the first dimple 3 so that the tip 7b of the bone forceps 7 sliding on the inner face 3c or the bottom portion 3b of the first dimple 3 can be trapped into the second dimple 8, it is possible to restrain the tip 7b of the bone forceps 7 from coming out of the opening portion 3a. Note, the second dimple 8 is configured so that an opening portion 8a of the second dimple 8 is larger than the tip 7b of the bone forceps 7, and so that a slant angle β2 of an inner face 8b of the second dimple 8 is larger than a slant angle β1 of the inner face 3c of the first dimple 3, whereby it is possible to obtain advantages of trapping the tip 7b of the forceps 7 in the second dimple 8, in comparison with the first dimples 3 shown in FIG. 3.

Also, as shown in FIG. 9, by providing the first dimples 3 in the side faces 1c of the bone plate 1 which are opposed to each other in the vertical direction to the longitudinal direction of the bone plate 1, the tip 7b of the bone forceps 7 can be substantially vertically abutted on the bottom portion 3b of the first dimple 3 concerned if a location at which the bone plate 1 is abutted on the bone is suitable. Thus, although there is a case where the tip 7b of the bone forceps 7 cannot be substantially vertically abutted on the front face 1b of the bone plate 1, it is possible to utilize the first dimple 3, formed in one of the side faces 1c, to grip the bone plate by the bone forceps 7, whereby the bone plate 1 and the diaphysis portion 6 are can be securely held.

Note, in Embodiment Mode 1, although there are shown the examples in which the first dimples 3 are provided in the front face 1a and the side faces 1c of the bone plate 1, the first dimples 3 may be provided in the rear face 1a of the bone plate 1 so that the front and rear faces of the bone plate 1 are reversed, so that the face which is abutted on the bone is defined as the front face 1b, and so that the dimples 3 provided in the rear face 1a can be used for gripping the bone plate by the bone forceps 7. In this case, it is preferable to form a concave seat face 2a in the rear face 1a of the bone plate 1 so that the head portion 4a of the screw 4 is fittingly received in the concave seat face 2a concerned.

As stated above, according to the bone plate 1 of Embodiment Mode 1 of the present invention, the converging-like first dimples 3 are provided in at least one of the faces except for the rear face 1a of the bone plate 1, the tip of the bone forceps 7 is engaged in any one of the first dimples 3, and then the tip thus engaged can be made to slide on the inner face 3c so as to be guided toward the bottom portion 3b, whereby the bone and the bone plate 1 can be gripped by the bone forceps 7.

Due to the fact that a surface of the conventional plate is specular-finished, it is difficult to use the forceps 7 to grip the bone and the plate, but it is possible to actively use the forceps 7 in the bone plate 1 of Embodiment Mode 1 of the present invention. Since the bone forceps 7 are provided with the tips smaller than those of other forceps, the use of the bone forceps 7 does not interfere with use of a perforation tool or another tool, and can make it possible to restrain invasion of the tips into tissues at minimum.

Also, since the centers O1 of the bottom portions 3b of the first dimples 3 are arranged near to the sides of the side faces 1c of the bone plate 1, which are in parallel to and symmetrical with the longitudinal direction of thereof, with respect to centers O2 of the opening portions 3a of the first dimples 3, it is possible to restrain the tip 7b of the bone forceps 7 from coming out of the opening portion 3a, whereby the bone plate 1 and the diaphysis portion 6 can be securely held.

Also, since the second dimples 8 are provided in the bottom portions 3b of the first dimple 3, the tip 7b of the bone forceps 7 sliding on the inner face 3c or the bottom portion 3b of the first dimple 3 can be trapped into a second dimple 8, it is possible to restrain the tip 7b of the bone forceps 7 from coming out of the corresponding opening portion 3a, whereby the bone plate 1 and the diaphysis portion 6 can be securely held.

Embodiment Mode 2

Figure 10:
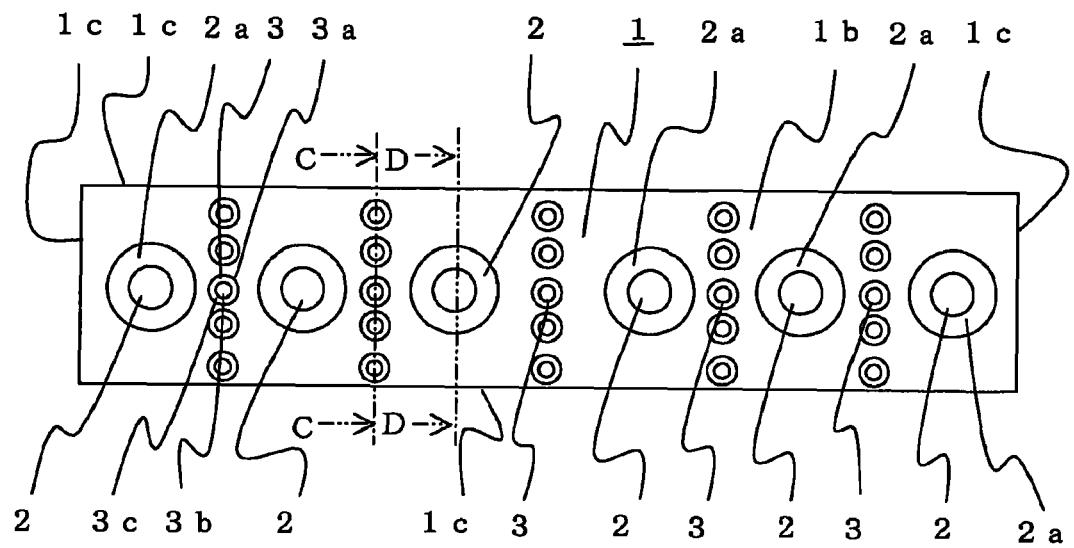
FIG. 10 are views showing a bone plate of Embodiment Mode 2 of the present invention, (a) being a bottom view, (b) being a cross-sectional view taken along the C-C line of the bone plate shown in FIG. 10(a), (c) being a cross-sectional view taken along the D-D line of the bone plate shown in FIG. 10(a).
Figure 10:
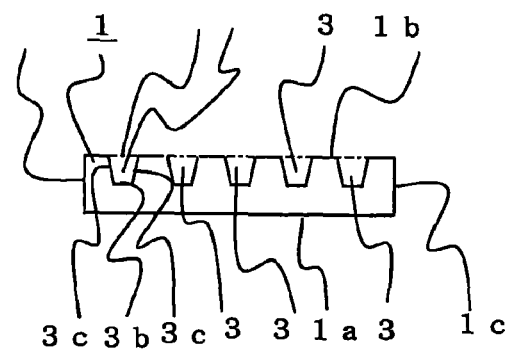
Figure 10:
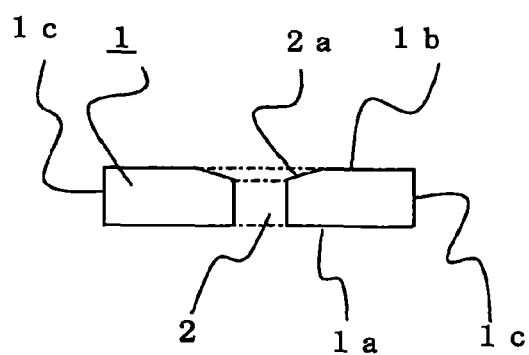

FIG. 10(a) is the bottom view showing a bone plate of Embodiment Mode 2 of the present invention, FIG. 10(b) is the cross-sectional view taken along the C-C line of the bone plate shown in FIG. 10(a), and FIG. 10(c) is the cross-sectional view taken along the D-D line of the bone plate shown in FIG. 10(a). In FIG. 10, the same elements or the corresponding elements are indicated by the same references as in FIGS. 1-9, and explanations of these elements are omitted.

Embodiment Mode 2 is only different from the Embodiment Mode 1 in that a plurality of first dimples 3 are arranged between through holes 2 adjacent to each other in a direction perpendicular to the longitudinal direction of a bone plate 1, and it is possible to obtain similar advantages to those of Embodiment Mode 1 except for another advantage obtained from the arrangement of the first dimples 3 as stated below.

In a conventional plate in which the first dimples 3 are not formed, a rigidity of a portion including a through hole becomes smaller in comparison with that of a portion between through holes adjacent to each other. For this reason, when the plate is bent in a longitudinal direction of the plate and in a vertical direction to a rear face, the bending of the plate is liable to occur at the portion including the through hole, and thus there is a problem that the through hole concerned may be deformed.

By contrast, according to the bone plate 1 of Embodiment Mode 2 of the present invention, the first dimples 3 are arranged between the through holes 2 adjacent to each other in the direction perpendicular to the longitudinal direction of the bone plate 1, so that a rigidity of the portion between the through holes 2 adjacent to each other becomes smaller in comparison with that of the portion including the through hole 2. Thus, when the bone plate 1 is bent in the longitudinal direction of the bone plate 1 and in the vertical direction to the rear face 1*a*, the bending of the bone plate 1 occurs at the portions in which the first dimples 3 are arranged, and thus it is possible to restrain the deformation of the through holes 2.

Embodiment Mode 3

Figure 11:
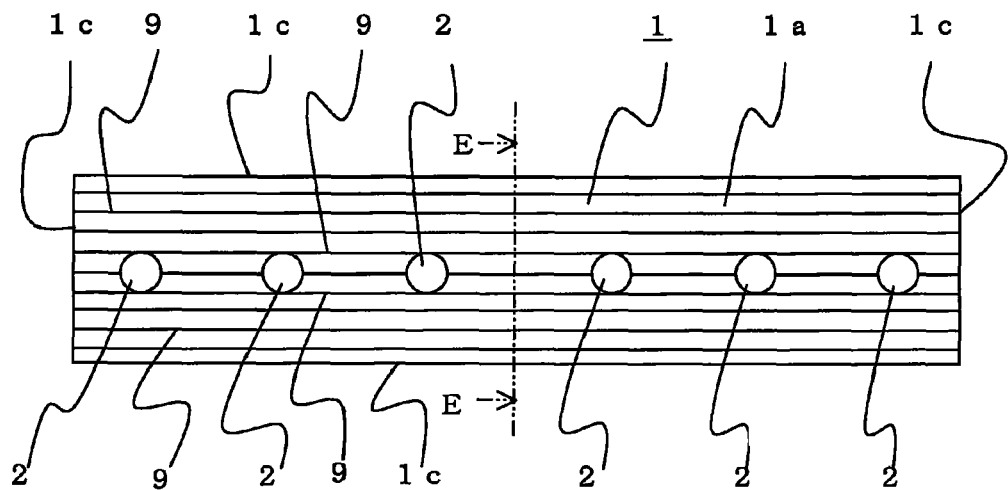
FIG. 11 are views showing a bone plate of Embodiment Mode 3 of the present invention, (a) being a bottom view, (b) being a cross-sectional view taken along the E-E line of the bone plate shown in FIG. 11(a), (c) being a cross-sectional view taken along the E-E line of the bone plate shown in FIG. 11(a), provided that it is subjected to a bending process.
Figure 11:
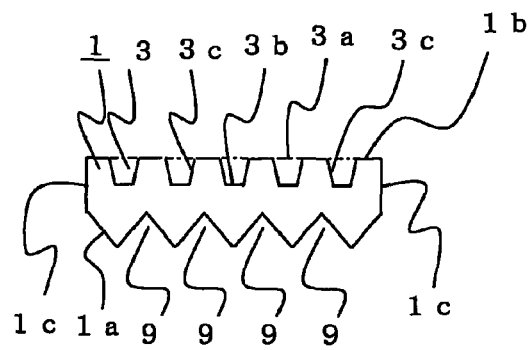
Figure 11:
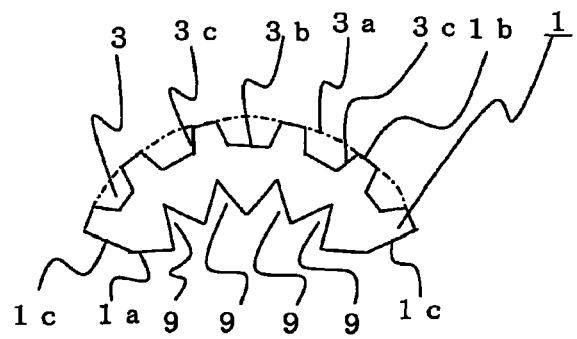

FIG. 11 (*a*) is the bottom view showing a bone plate of Embodiment Mode 3 of the present invention, FIG. 11(*b*) is the cross-sectional view taken along the E-E line of the bone plate shown in FIG. 11(*a*), and FIG. 11(*c*) being the cross-sectional view taken along the E-E line of the bone plate shown in FIG. 11(*a*), provided that it is subjected to the bending process. In FIG. 11, the same elements or the corresponding elements are indicated by the same references as in FIGS. 1-10, and explanations of these elements are omitted.

As shown in FIGS. 11(*a*) and 11(*b*), a plurality of longitudinal grooves 9 comprising hollows are formed in a rear face 1*a* of a bone plate 1 in a longitudinal direction of the bone plate 1. Note, in Embodiment Mode 3, although the longitudinal grooves 9 have a V-shape in the cross-sectional view, the longitudinal grooves 9 should not be limited to this shape and the number thereof.

Embodiment Mode 3 is only different from the Embodiment Modes 1 and 2 in that the longitudinal grooves 9 are formed in the rear face 1*a* of the bone plate 1, and it is possible to obtain similar advantages to those of Embodiment Modes 1 and 2 except for another advantage obtained from the longitudinal grooves 9 as stated below.

Incidentally, when a plate is applied to a surface of a bone so as to be directly contacted with and pressed against the bone, there is a possibility of preventing a blood circulation in a bone cortex therebeneath over a long time. Reproduction of the bone and resumption of the blood circulation are slow, and the bone cortex of the portion pressed by the plate may become porous.

By contrast, in Embodiment Mode 3, since the longitudinal grooves 9 are formed in the rear face 1*a* of the bone plate 1 to thereby reduce a contact area between the bone and the bone plate 1, damage of the capillaries in the bone membrane is small, a blood circulation in the bone cortex is relatively improved, and a bone atrophy caused directly beneath the bone plate 1 can be lessened.

Also, as shown in FIG. 11(*c*), a bending of the bone plate 1 in the direction perpendicular to the longitudinal direction of the bone plate 1 to define the rear face 1*a* as a concave face and a bending of the bone plate 1 in a twisted direction are made possible so that the rear face 1*a* of the bone plate 1 can be curved so as to conform with a shape of a broken bone for abutment of the bone plate thereon. In this case, since tensile stresses occur in the front face 1*b* of the bone plate 1 so that the front face 1*b* is defined as a curved face, it is possible to further enhance the aforesaid advantages derived from the first dimples 3, in comparison with the conventional plate which it is difficult to hold with the tip 7*b* of the bone forceps 7.

Also, in a bone-setting operation, with definition of the fracture line 5 as a boundary, after one of the pieces of broken bone is fixed to the bone plate 1, the other piece of broken bone is fixed to the bone plate 1. At this time, if there is a gap between both the pieces of broken bone at the fracture line 5, it is necessary to relatively move the other piece of broken bone with respect to the bone plate 1. In this case, it is possible to easily slide the other piece of broken bone in the longitudinal direction of the bone plate 1 due to the longitudinal grooves 9 formed in the rear face 1*a* of the bone plate 1, whereby the gap between both the pieces of broken bone can be narrowed with facility.

Note, in Embodiment Mode 3, although the longitudinal grooves 9 are formed in the rear face 1*a* of the bone plate 1, lateral grooves may be formed in the rear face 1*a* of the bone plate 1 in the direction perpendicular to the longitudinal direction of the bone plate 1. Thus, a bending of the bone plate 1 in the longitudinal direction of the bone plate 1 to define the rear face 1*a* as a concave face and a bending of the bone plate 1 in a twisted direction are made possible so that the rear face 1*a* of the bone plate 1 can be curved so as to conform with a shape of a broken bone for abutment of the bone plate thereon.

Also, in a bone-setting operation, with definition of the fracture line 5 as a boundary, after one of the pieces of broken bone is fixed to the bone plate 1, when there is not a gap between the pieces of broken bone in the fracture line 5, the other piece of broken bone is restrained from being slid in the longitudinal direction of the bone plate 1 due to the lateral grooves formed in the rear face 1*a* of the bone plate 1, whereby both the pieces of broken bone can prevented from being separated from each other.

Embodiment Mode 4

Figure 12:
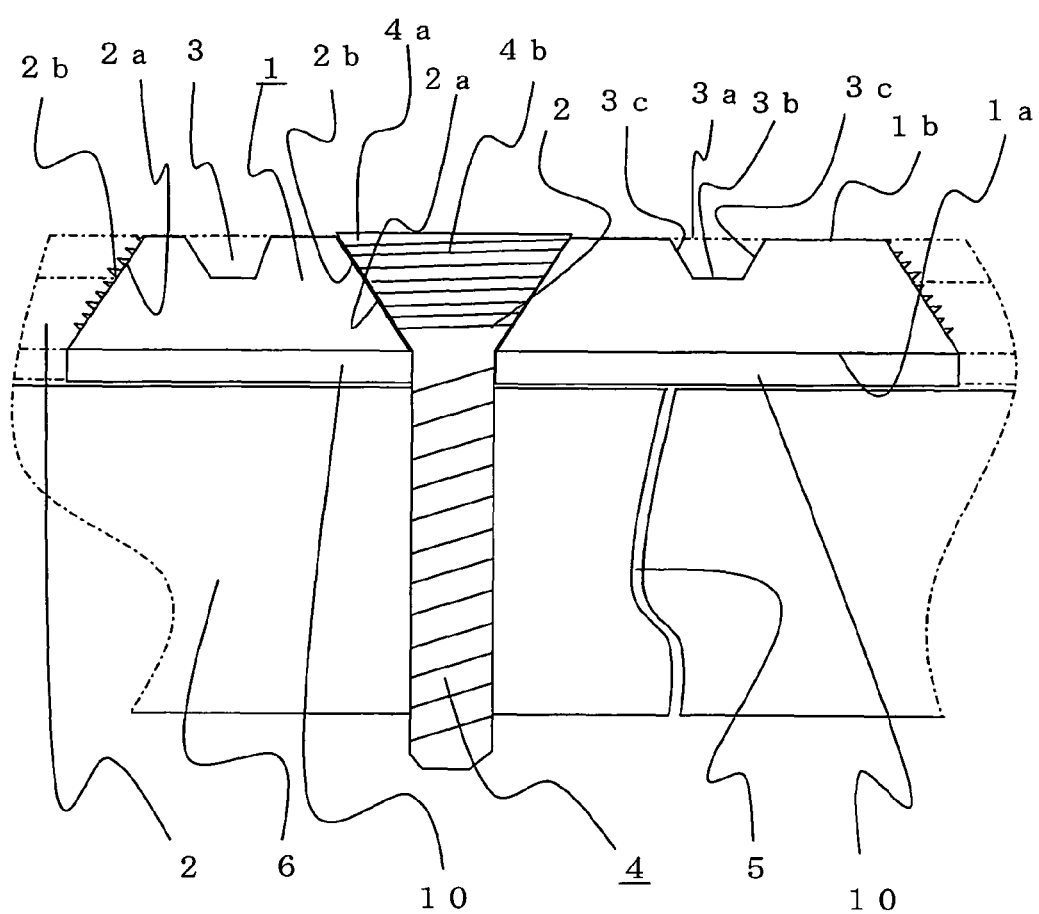
FIG. 12 is a partial cross-sectional view showing the state in which a bone plate of Embodiment Mode 4 of the present invention is applied to a bone.

FIG. 12 is a partial cross-sectional view showing the state in which a bone plate of Embodiment Mode 4 of the present invention is applied to a bone. In FIG. 12, the same elements or the corresponding elements are indicated by the same references as in FIGS. 1-11, and explanations of these elements are omitted.

The rear face 1*a* of the bone plate 1 is coated with a biological biodegradable/bioabsorbable membrane 10. Note, in Embodiment Mode 4, for the biological biodegradable/bioabsorbable membrane 10, poly-L-lactic acid is used.

Also, a male thread 4*b*, which is threadedly engaged with the bone plate 1, is formed around a peripheral face of the head portion 4*a* of the screw 4, and a female thread 2*b*, which is threadedly engaged with the male thread 4*b* of the screw 4, is formed in the through hole 2.

Embodiment Mode 4 is only different from Embodiment Modes 1, 2 and 3 in that the rear face 1*a* of the bone plate 1 is coated with the biological biodegradable/bioabsorbable membrane 10, and it is possible to obtain similar advantages to those of Embodiment Modes 1 and 2 except for another advantage obtained from the biological biodegradable/bioabsorbable membrane 10 as stated below.

Incidentally, polylactic acid is a biological biodegradable/bioabsorbable polymer which is hydrolyzed in a living body by acids and alkalis so that it is degraded to lactic acids, which is start material, and lactic acids are metabolized and excreted from the living body. Since lactic acids exit in the living body, and are nonpoisonous, polylactic acids are hopefully expected for medical materials. Also, among lactic acids, there are D-lactic acid and L-lactic acid, and thus three kinds of polylactic acids: poly-D-lactic acid, poly-D, L-lactic acid and poly-L-lactic acid (racemic modification) are produced. At present, poly-L-lactic acid is used for the medical materials.

The biological biodegradable/bioabsorbable membrane 10, with which the rear face 1*a* of the bone plate 1 is coated, maintains a necessary strength over a period of time when a broken bone is healed. Thereafter, the biological biodegradable/bioabsorbable membrane 10 is degraded and absorbed as soon as possible, and thus the surface of the bone is prevented from being pressed by the bone plate 1 over a long time, so that a blood circulation cannot be impeded in the bone cortex. Namely, the poly-L-lactic acid membrane is absorbed by the bone near the fracture location, so that a provisional bone formation can be facilitated, and so that a bone atrophy can be prevented.

Note, when the biological biodegradable/bioabsorbable membrane 10, with which the rear face 1a of the bone plate 1 is coated, is degraded and absorbed, a clearance, which corresponds to the thickness of the biological biodegradable/bioabsorbable membrane 10 is defined between the rear face 1a of the bone plate 1 and the bone.

Due to this clearance, if the screw 4, in which the male thread 4b is not formed around the peripheral face of the head portion 4a, is used, the screw 4 merely passes through the through hole 2 of the bone plate 1 without being fixed to the bone plate, and thus a play is caused at the junction between the bone plate 1 and the through hole 2 so that the inherent function of the plate cannot be obtained.

Thus, in Embodiment Mode 4, since the male thread 4b, which is threadedly engaged with the bone plate 1, is formed around the peripheral face of the head portion 4a of the screw 4, and since the female thread 2b, which is threadedly engaged with the male thread 4b of the screw 4, is formed in the through hole 2, although the biological biodegradable/bioabsorbable membrane 10 is degraded and absorbed to thereby define the clearance, it is possible to maintain the inherent function of the bone plate 1 because the screw 4 is threadedly engaged with the through hole 2 of the bone plate 1.

The invention claimed is:

1. A bone plate, comprising:
a bone plate body extending along a centrally-disposed longitudinal axis and laterally therefrom to form a substantially rectangular configuration, the bone plate body including:
a rear face adapted to be abutted on a bone;
a front face opposed to said rear face; and
side faces extending between side edges of said rear face and side edges of said front face,
said bone plate having a plurality of through holes, each through hole extending between said rear face and said front face for receiving a screw to fix the bone plate on the bone and disposed approximately centrally of the bone plate body as viewed in lateral cross-section, the plurality of through holes arranged longitudinally along the longitudinal axis to form a straight line of through holes disposed apart from one another,
wherein said bone plate has at least one first blind dimple provided in at least one of said front face and said side faces except for said rear face,
wherein said first blind dimple is adapted to be gripped by a first acute gripping tip of a pair of bone forceps while a second acute gripping tip is abutted to the bone,
wherein said first blind dimple is configured so as to converge from an opening portion thereof toward a bottom portion thereof, whereby said first acute gripping tip of said bone forceps can slide toward said bottom portion;
wherein the at least one first blind dimple is located centrally along the longitudinal axis and between two consecutive ones of the plurality of through holes; and
wherein said rear face has a longitudinal groove formed in a longitudinal direction of said bone plate.

2. The bone plate as set forth in claim 1, wherein the bottom portion of said first dimple is defined as a converging point of an inner face of said first blind dimple.

3. A bone plate, comprising:
a bone plate body extending along a centrally-disposed longitudinal axis and laterally therefrom to form a substantially rectangular configuration, the bone plate body including:
a rear face adapted to be abutted on a bone;
a front face opposed to said rear face; and
side faces extending between side edges of said rear face and side edges of said front face,
said bone plate having a plurality of through holes, each through hole extending between said rear face and said front face for receiving a screw to fix the bone plate on the bone and disposed approximately centrally of the bone plate body as viewed in lateral cross-section, the plurality of through holes arranged longitudinally along the longitudinal axis to form a straight line of through holes disposed apart from one another,
wherein said bone plate has at least one first blind dimple provided in at least one of said front face and said side faces except for said rear face,
wherein said first blind dimple is adapted to be gripped by a first acute gripping tip of a pair of bone forceps while a second acute gripping tip is abutted to the bone,
wherein said first blind dimple is configured so as to converge from an opening portion thereof toward a bottom portion thereof, whereby said first acute gripping tip of said bone forceps can slide toward said bottom portion;
wherein the at least one first blind dimple is located centrally along the longitudinal axis and between two consecutive ones of the plurality of through holes; and
wherein said rear face has a lateral groove formed in a direction perpendicular to a longitudinal direction of said bone plate.

4. The bone plate as set forth in claim 1, wherein said rear face is coated with a biological biodegradable/bioabsorbable membrane.

5. The bone plate as set forth in claim 1, wherein a female thread, which is threadedly engaged with a male thread of a head of a screw, is formed in said through hole.

6. A bone plate, comprising:
a bone plate body extending along a centrally-disposed longitudinal axis and laterally therefrom to form a substantially rectangular configuration, the bone plate body including:
a rear face adapted to be abutted on a bone;
a front face opposed to said rear face; and
side faces extending between side edges of said rear face and side edges of said front face,
said bone plate having a plurality of through holes, each through hole extending between said rear face and said front face for receiving a screw to fix the bone plate on the bone and disposed approximately centrally of the bone plate body as viewed in lateral cross-section, the plurality of through holes arranged longitudinally along the longitudinal axis to form a straight line of through holes disposed apart from one another,
wherein said bone plate has at least one first blind dimple provided in at least one of said front face and said side faces except for said rear face,
wherein said first blind dimple is adapted to be gripped by a first acute gripping tip of a pair of bone forceps while a second acute gripping tip is abutted to the bone,
wherein said first blind dimple is configured so as to converge from an opening portion thereof toward a bottom portion thereof, whereby said first acute gripping tip of said bone forceps can slide toward said bottom portion;
wherein the at least one first blind dimple is located centrally along the longitudinal axis and between two consecutive ones of the plurality of through holes; and
wherein a second blind dimple is provided in the bottom portion of said first blind dimple so that the first acute gripping tip of said bone forceps can be trapped into the second blind dimple.

* * * * *